(12) United States Patent
Lechner et al.

(10) Patent No.: US 10,335,247 B2
(45) Date of Patent: Jul. 2, 2019

(54) UNIVERSAL INSTRUMENT OR INSTRUMENT SET FOR COMPUTER GUIDED SURGERY

(71) Applicant: Brainlab AG, Munich (DE)

(72) Inventors: Christian Lechner, Jessenwang (DE); Claus Schaffrath, Rosenheim (DE)

(73) Assignee: Brainlab AG, Munich (DE)

( * ) Notice: Subject to any disclaimer, the term of this patent is extended or adjusted under 35 U.S.C. 154(b) by 297 days.

(21) Appl. No.: 15/198,998

(22) Filed: Jun. 30, 2016

(65) Prior Publication Data

US 2017/0000583 A1 Jan. 5, 2017

Related U.S. Application Data

(63) Continuation of application No. 11/015,297, filed on Dec. 17, 2004, now Pat. No. 9,393,039.

(Continued)

(30) Foreign Application Priority Data

Dec. 17, 2003 (DE) .................................. 103 59 296
Apr. 30, 2004 (EP) .................................. 04 010 353

(51) Int. Cl.
*A61B 17/00* (2006.01)
*A61B 90/00* (2016.01)
*A61B 17/3207* (2006.01)
*A61B 34/20* (2016.01)
*A61B 90/94* (2016.01)
(Continued)

(52) U.S. Cl.
CPC ........ *A61B 90/39* (2016.02); *A61B 17/00234* (2013.01); *A61B 17/1671* (2013.01);
(Continued)

(58) Field of Classification Search
CPC ........... A61B 2017/00455; A61B 2017/00725; A61B 2034/2055; A61B 2090/3983; A61B 34/20
See application file for complete search history.

(56) References Cited

U.S. PATENT DOCUMENTS 2,209,425 A * 7/1940 Steinhilber .............. A43D 5/02
12/126
3,504,776 A 4/1970 Misenti
(Continued)

FOREIGN PATENT DOCUMENTS

DE 20203439 U1 7/2003

OTHER PUBLICATIONS

European Search Report for Application No. 04010353.3 dated Aug. 19, 2004.

(Continued)

*Primary Examiner* — Gregory A Anderson
(74) *Attorney, Agent, or Firm* — Tucker Ellis LLP

(57) ABSTRACT

The invention relates to an instrument for use in computer guided surgery. The instrument includes a shaft and a reference element adapter, wherein the reference element adapter is directly couplable to the shaft and rotatable about the shaft. A selectively operable mechanical retainer provides retention of the reference element adapter to an instrument shaft adapting interface of the instrument shaft. The instrument also includes a reference element orientating mechanism arranged at an interface between the instrument shaft adapting interface and the reference element adaptor. The reference element orienting mechanism is capable of fixing at least one angular position of the reference element. The instrument also includes a grip piece interface on the instrument shaft, and a grip piece is selectively couplable to the grip piece interface.

10 Claims, 6 Drawing Sheets

Related U.S. Application Data

(60) Provisional application No. 60/579,574, filed on Jun. 14, 2004.

(51) Int. Cl.
  *A61B 34/10* (2016.01)
  *A61B 17/16* (2006.01)

(52) U.S. Cl.
  CPC ...... *A61B 17/320708* (2013.01); *A61B 34/10* (2016.02); *A61B 34/20* (2016.02); *A61B 90/36* (2016.02); *A61B 90/94* (2016.02); *A61B 2017/00261* (2013.01); *A61B 2017/00455* (2013.01); *A61B 2017/00464* (2013.01); *A61B 2017/00477* (2013.01); *A61B 2017/00725* (2013.01); *A61B 2034/2055* (2016.02); *A61B 2090/3983* (2016.02)

(56) References Cited

U.S. PATENT DOCUMENTS

| | | |
|---|---|---|
| 6,021,343 A | 2/2000 | Foley et al. |
| 6,556,857 B1 | 4/2003 | Estes et al. |
| 6,856,828 B2 * | 2/2005 | Cossette ............ A61B 90/39 600/429 |
| 7,017,238 B2 | 3/2006 | Messina |
| 7,237,556 B2 | 7/2007 | Smothers et al. |
| 2002/0035321 A1 | 3/2002 | Bucholz et al. |

OTHER PUBLICATIONS

Lemke et al., Computer Assisted Radiology and Surgery, Jun. 23-26, 1999, Paris (France).

* cited by examiner

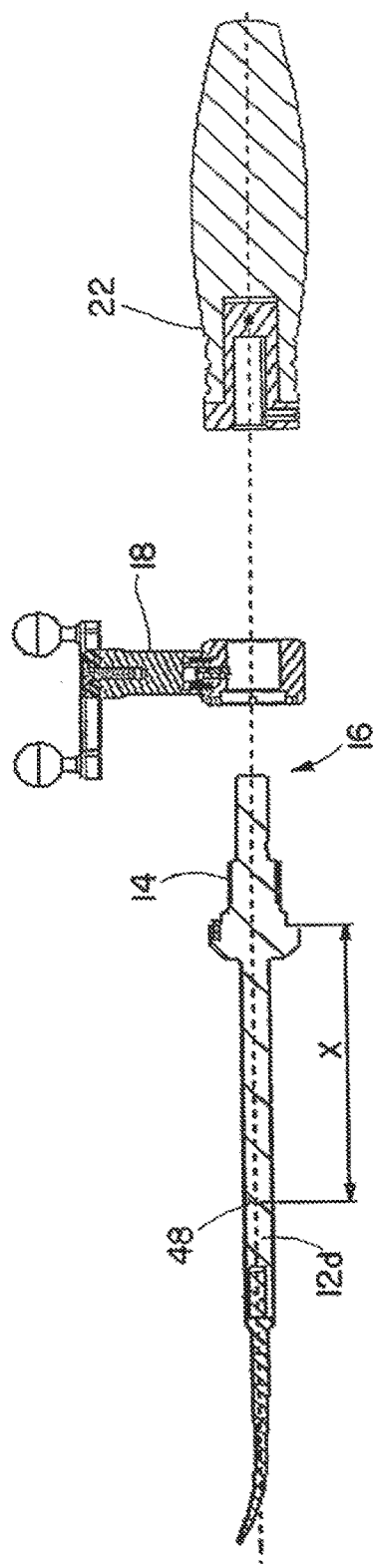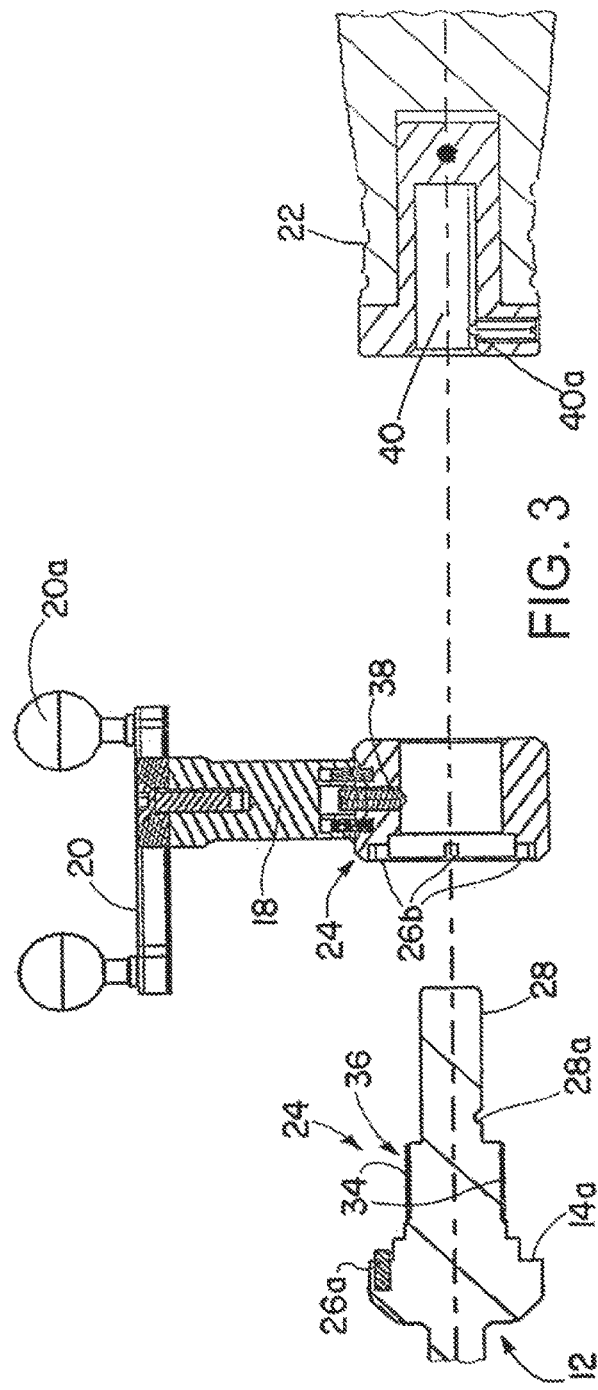

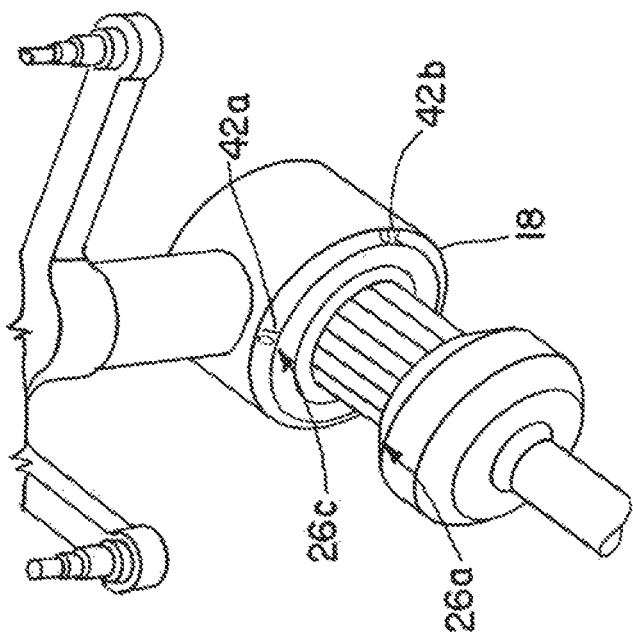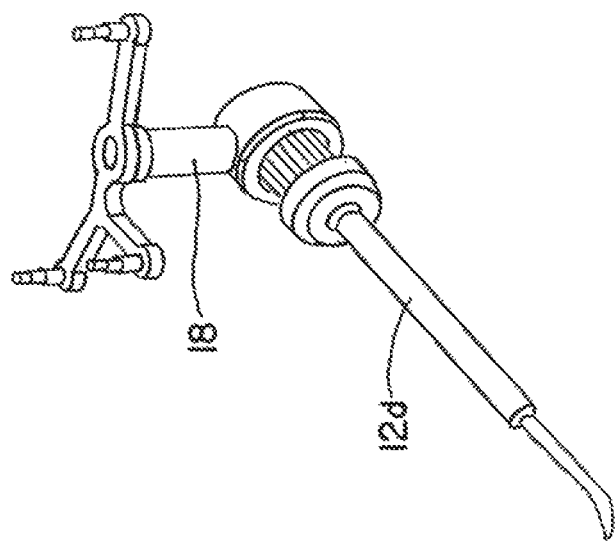
FIG. 5

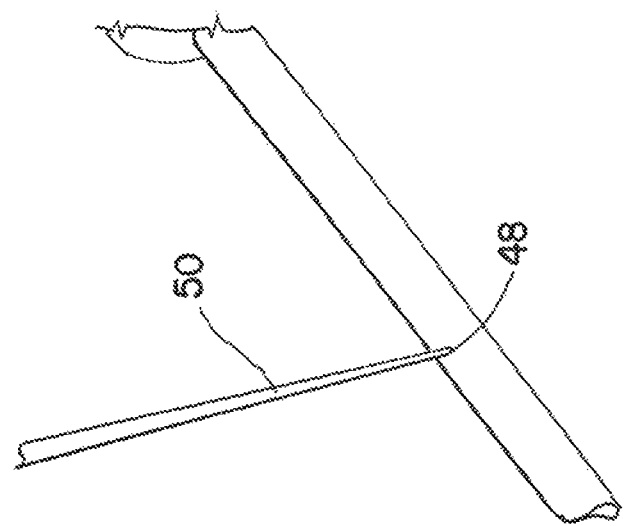
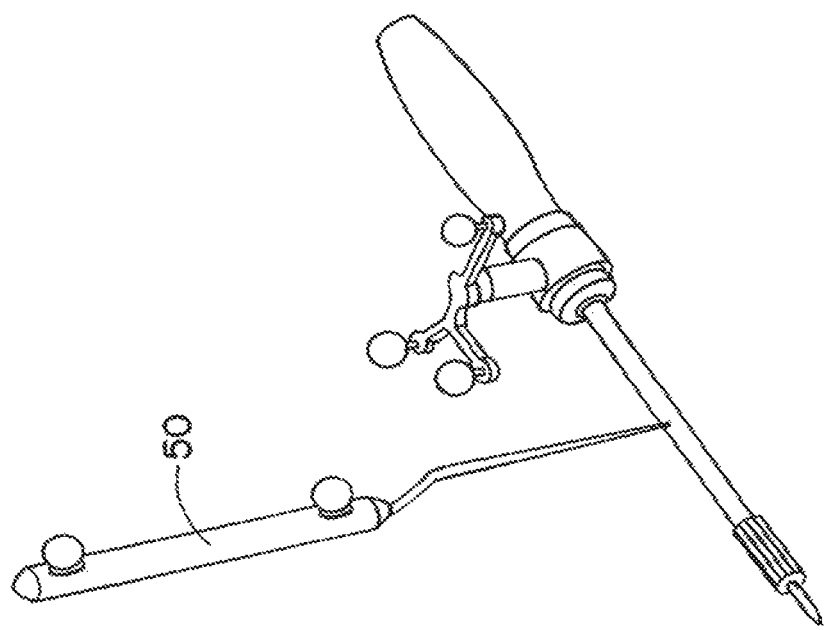
FIG. 7

UNIVERSAL INSTRUMENT OR INSTRUMENT SET FOR COMPUTER GUIDED SURGERY

CROSS-REFERENCE TO RELATED APPLICATIONS

This application is a continuation of application Ser. No. 11/015,297, filed on Dec. 17, 2004 (now U.S. Pat. No. 9,393,039), application Ser. No. 11/015,297 claims the benefit of U.S. Provisional Application No. 60/579,574 filed on Jun. 14, 2004, application Ser. No. 11/015,297 claims priority under 35 U.S.C. § 119 to German patent application DE 103 59 296.3 filed on Dec. 17, 2003, and application Ser. No. 11/015,297 claims priority under 35 U.S.C. § 119 to patent application EP 04 010 353.3 filed on Apr. 30, 2004.

TECHNICAL FIELD

The present invention relates to instruments used in computer guided surgery and, more particularly, to a universal instrument or instrument set for use in computer-guided surgery.

BACKGROUND

Computer guided surgery (CGS) is a tool often used by surgeons to assist during surgical procedures. When using CGS, the bone structure and/or the internal anatomy of a patient is known to a navigation system following a reading-in procedure. CGS, via a display, provides visual feedback to the surgeon of an area of interest in the patient with respect instruments, such as awls, chisels, bodkins and/or other devices (e.g., stability rods, tools, clamps and the like) as well as the position of the instruments in the area of interest. The surgeon uses the visual feedback to place or otherwise position the instruments on or in the area of interest to achieve a desired result and/or position of the instrument with respect to the area of interest.

In CGS, instruments are calibrated intra-operatively on or in the area of interest of the patient. Once calibrated, the instrument can be navigated to achieve the desired position of the instrument with respect to the area of interest. To this end, an instrument referencing device, such as a reference star, is clamped or otherwise attached to the corresponding instrument, and the reference star, in conjunction with a particular calibration block (e.g., an instrument calibration matrix (ICM)—if necessary), is used to calibrate the instrument within a work space. All in all, this calibration step can be very time-consuming and inconvenient for the user. Moreover, there exists a possibility that the referencing device can come loose after calibration, i.e., during application of the instrument, thereby distorting the calibration and thus the accuracy of navigation. In addition, the calibration itself can conceal possible sources of error that surface later, resulting in further navigation inaccuracies. If the user is not aware of these inaccuracies in the instrument calibration, injuries to the patient are possible.

In CGS on the spine, navigation is mainly used to accurately place implant screws into the pediculi of the vertebra, without injuring the spinal cord or spinal nerves or other vital organs or blood vessels in the surrounding area. The spinal instruments serve to prepare and open up the pediculus in order to correctly insert the pedical screws. Pre-calibrated instruments generally are required for CGS. By pre-calibrating the instruments, the chance for calibration errors introduced by the user are minimized or eliminated altogether.

A rotatable instrument adaptor for spinal CGS is known from U.S. Pat. No. 6,021,343 to Foley et al. This solution includes an intermediate piece adaptor having a rotatably mounted reference star that is recognised by the navigation system. The adaptor includes a quick-release lock at each of its two ends. On one end, different instrument tips can be attached to the adapter, and on the other end different grips or drills can likewise be attached. The intermediate piece adaptor then can be used to navigate different spinal instruments, which, however, have to be rotationally symmetrical in order to be correctly displayed.

U.S. Pat. No. 6,556,857 to Estes et al. mentions how a rotatable intermediate piece adaptor can have a catch mechanism in a position known by software. However, the embodiment and functionality of such a catch mechanism for navigation are not described.

BRIEF SUMMARY OF EXAMPLE EMBODIMENTS

The present invention provides an instrument or an instrument set for use in CGS that overcomes one or more of the disadvantages and shortcomings of the prior art. For instance, the invention enables a high level of accuracy to be attained when attaching a reference element relative to the instrument, thus enabling a high level of accuracy in software recognition and navigation of the instrument. The invention also enables implementation of pre-calibrated rotationally asymmetrical instruments into computer-guided surgery systems.

According to the invention, a reference element adaptor is arranged directly on the instrument shaft, such that the adapter can rotate about the shaft. In this way, the present invention rises above the known "intermediate piece adaptor" solutions. This enables a greater accuracy to be achieved, since an additional interface is not present between the instrument tip and the reference adaptor and, therefore, an additional source of error is minimized or eliminated. The angular accuracy of the reference element position relative to the instrument axis, in particular, is improved.

The reference element adaptor is arranged on an instrument shaft adapting interface of the instrument shaft. The instrument shaft adapting interface and the portion of the reference element adaptor surrounding the instrument shaft adapting interface can include a selectively operable mechanical retainer, such as a detachable angular rotational catch. This angular rotational catch can be formed such that the reference element always maintains the same angle on the instrument shaft during operation, while providing the option of altering the angle, if desired. To this end, the angular rotational catch includes a surmountable frictional or positive coupling, such as a ball-thrust piece on a wrap-around portion of the reference element adaptor. The coupling or catch can engage with one or more circumferentially distributed, longitudinal notches of the instrument shaft adapting interface.

In accordance with the invention, there is provided an instrument for use in computer guided surgery, including: a shaft; and a reference element adapter, wherein the reference element adapter is directly couplable to the shaft and rotatable about the shaft.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 2 illustrates a longitudinal sectional view of a surgical instrument configured in accordance with an embodiment of the invention.

FIG. 3 illustrates an enlargement of the view of FIG. 2 in an area where a reference element is attached to the instrument.

FIG. 5 illustrates an isometric view and an enlarged cutaway view that show a reference element attached to an instrument shaft in accordance with an embodiment of the invention.

FIG. 7 illustrates an isometric view and a cutaway enlargement for software recognition of instruments in accordance with an embodiment of the invention.

DETAILED DESCRIPTION OF EXAMPLE EMBODIMENTS

Figure 1:
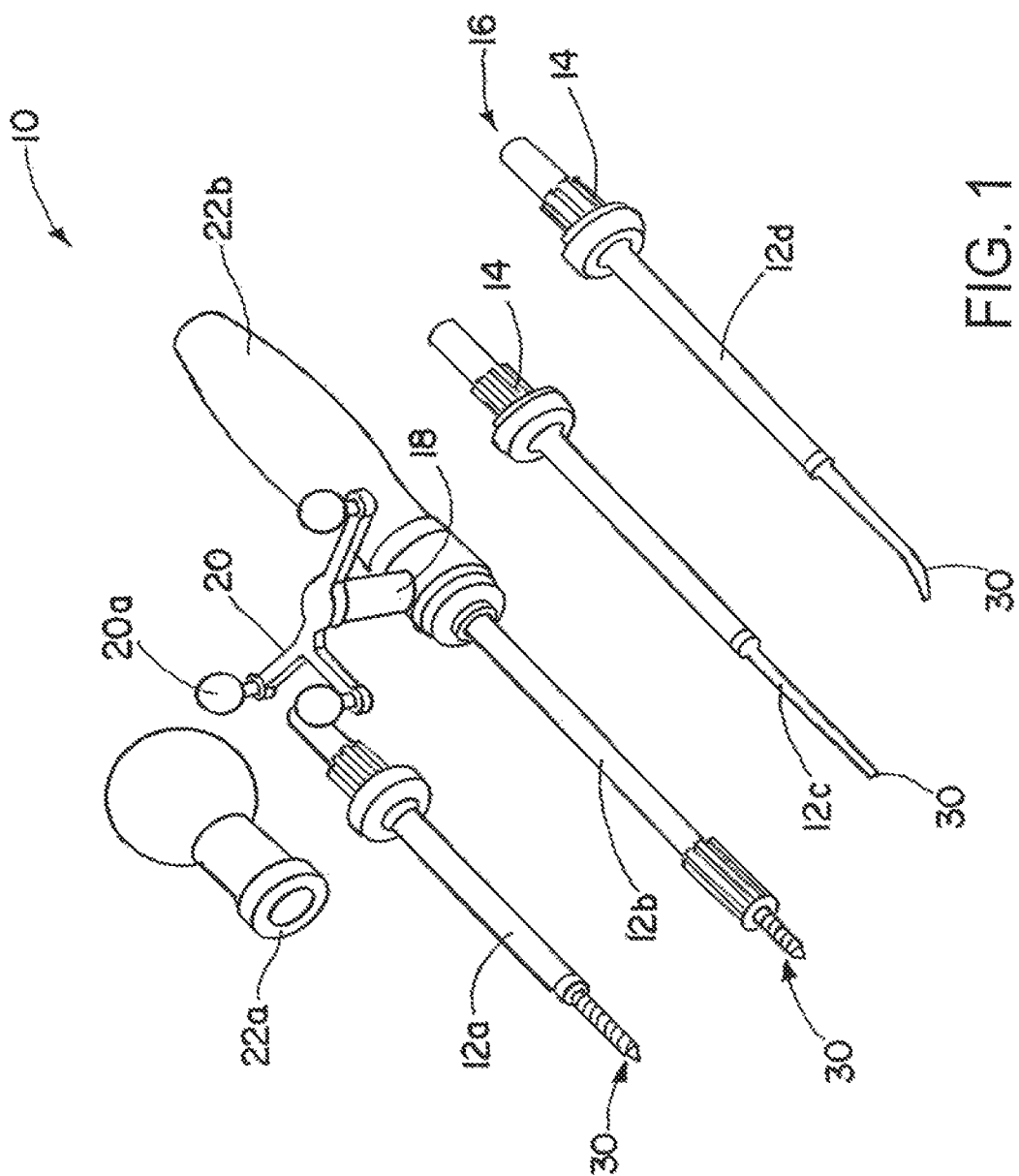
FIG. 1 illustrates an isometric view of a set of different spinal instruments, including an awl and a bodkin, both of which are configured in accordance with an embodiment of the present invention.

The present invention relates to an instrument for use in computer guided surgery, wherein a reference element adapter is directly arranged on the instrument shaft and rotatable about the instrument shaft. FIG. 1 illustrates the application of the present invention to various instruments of an instrument set 10 used in computer-guided surgery. Different instrument shafts 12a, 12b, 12c, 12d (collectively referred to as shaft 12) are shown, wherein each shaft pertains to a different instrument, e.g., an awl, a bodkin, etc. Depending on the required application of the instrument, the instrument and/or it's respective shaft 12 can have different shapes and/or lengths with respect to other instruments in the set, and the instruments need not necessarily be rotationally symmetrical, as can be seen from the instrument shafts 12c and 12d.

Each instrument shaft 12a-12d has a uniform adapting interface 14 at a proximal end 16 of the shaft. FIGS. 2 and 3, which will be discussed in more detail below, illustrate exploded sectional views of the uniform adapting interface 14. A rotatable reference element adapter 18 of each instrument accepts a reference element 20, such as a reference star, which can be provided with passive markers 20a or, alternatively, with active markers (not shown), such that the instrument can be tracked by the navigation system (not shown). Furthermore, FIG. 1 also illustrates examples of different grip pieces 22a, 22b.

The rotatable reference element adapter 18 permits a user, such as a surgeon, to arrange the reference element 20 in one of a plurality of positions such that the reference element 20 is in view the navigation system cameras (not shown) regardless of the orientation of the instrument. Should the surgeon wish to position the instrument in such a way that the reference element 20 is not in view of the cameras, the surgeon can reposition the reference element via the reference element adapter 18, without the need to recalibrate the instrument in the navigation system.

In accordance with the invention, and with further reference to FIG. 3, an instrument shaft can be formed such that the instrument shaft adapting interface 14 includes a reference axial stopper area 14a for the reference element adaptor 20. In this way, a predetermined axial position for the reference element adaptor 20 can be set. Additionally, and as will be discussed in more detail below, at least one reference element orientating mechanism 24 is arranged at the interface between the instrument shaft adapting interface 14 and the reference element adaptor 20. The reference element orientating mechanism 24 can fix one or more particular angular positions of the reference element adaptor 20 with respect to the instrument shaft 12, and such reference element orientating mechanism 24 creates a selectively settable and detachable catch between the instrument shaft adapting interface 14 and the reference element adaptor 20.

In accordance with one embodiment of the invention, the reference element orientating mechanism 24 includes an orientating pin 26a provided on the reference axial stopper area 14a of the instrument, and at least one orientating slit 26b is provided on a wrap-around portion of the reference element adaptor 20. Additionally, a grip piece interface 28 is provided on the instrument shaft 12, in particular on or integral with the instrument shaft adapting interface 14. A grip piece 22a, 22b can be selectively coupled or attached to said grip piece interface 28 via a non-rotational quick-release lock, said grip piece limiting and/or inhibiting an axial movement of the reference element adaptor 18.

An instrument formed in accordance with the invention can be configured such that the reference element adaptor 18 and the instrument shaft 12, in particular the instrument shaft adapting interface 14, include an aligning mechanism that prevents the reference element adaptor 18 from being placed onto the instrument shaft in a reverse or "backwards" position. This can be achieved, for example, by the particular engagement of the adapter interface 14 and the reference element adapter 18 being formed on only one side of each respective component and/or via the orientating pins 22a and orientating slits 22b discussed above.

In accordance with another embodiment of the invention, the instrument shaft 12 includes at least one marking point arranged instrument-specifically, i.e., the marking point is arranged in a unique position or location for each type of instrument. For example, and as will be described in more detail below, a marking point, such as an indentation, can be formed on a location along the instrument shaft 12, wherein the location of the marking point is used by the navigation system to identify the particular instrument being used by the surgeon. For example, and as will be described in more detail below, the location of the marking point along the shaft can be in a unique location for each type of instrument. To determine the instrument type, a pointer or other device that can be tracked by the navigation system is placed on or inserted into the marking point and, based on the ascertained location of the marking point with respect to the reference element 20 of the instrument, the type of instrument can be ascertained.

The instrument shaft 12 and/or a tip 30 of the instrument can be configured either to be rotationally symmetrical or rotationally asymmetrical. The embodiment described above, including the orientating means, e.g., the orientating pins 26a and the orientating slits 26b, is particularly suitable for rotationally asymmetrical instruments.

The instrument set 10 in accordance with an embodiment of the invention includes at least two instruments that have uniform grip piece interfaces 28 for accepting different grip pieces 22a, 22b. The grip pieces themselves can have different interfaces, e.g., different grips or different shapes. Furthermore, the instrument shaft 12 of different instruments types can include marking points which are arranged instrument-specifically, thereby permitting identification of the instruments in the set 10 by software as was described above, e.g., the marking points to be tracked by-a pointer of a surgical navigation system.

Each instrument of the instrument set 10 can be a spinal instrument, such as, for example, an awl, a chisel, a bodkin, etc. The instrument set can include one or more of each of the aforementioned instruments. It should be appreciated, however, that the instrument set can include instruments related to other surgical disciplines, such as instruments related to trauma and/or orthopaedic treatment (hip, knee, etc.) and such instruments can be utilized with surgical navigation and/or computer-guided surgery systems. The instruments can be rotationally symmetrical or rotationally asymmetrical.

With reference to FIGS. 1, 2 and 3, the invention will now be described in more detail. The reference element adaptor 18 is arranged directly and rotatably on the instrument shaft 12. More specifically, the reference element adapter 18 is arranged on the instrument shaft adapting interface 14, which is uniformly configured for all instruments in an instrument set 10. In the embodiment shown, the instrument shaft adapting interface 14 includes a selectively operable mechanical retainer having latching notches 34 on a cylindrical surface 36 of the shaft 12. The notches 34 are circumferentially distributed and substantially equidistant around the cylindrical surface 36, e.g. twelve latching notches at a distance of 30 degrees apart. Other selectively operable mechanical retainers are possible, such as, for example, releasable clasps or the like. Additionally, and as was noted above, the instrument shaft adapting interface 14 includes a reference area 14a forming an axial stopper for the reference element adaptor 18.

In the direction of its inner axial passageway, the reference element adaptor 18 includes a centric ball-thrust piece 38 that can latch into one of the latching notches 34 and, thus, prevent the reference element adaptor 18 from being unintentionally rotated, e.g., rotated with respect to the shaft 12.

When assembling the instrument configured in accordance with the invention, the rotatable reference element adaptor 18 is placed directly on the instrument shaft adapting interface 14 of the instrument shaft 12. Due to the configuration of the reference element adaptor 18, it only can be axially placed on the shaft 12 in a specific orientation. For example, if the reference element adapter 18 is improperly placed on the shaft 12, e.g., placed on the shaft in the reverse direction, the centric ball thrust piece 38 of the reference element adapter 18 will not interface with the notches 34 and, therefore, will not lock into place. The reference element adaptor 18 has reference element 20, which can include passive markers 20a or active markers (not shown), that are utilized by the navigation system to track the instrument.

Placing the reference element adaptor 18 directly onto the instrument shaft 12, e.g., on the instrument shaft adapting interface 14, provides for greater accuracy of the navigated instrument axis when compared to instruments on which additional interfaces are provided. The axial clearance of the reference element adapter 18 is limited by the grip pieces 22a, 22b, which can be coupled to the proximal end 16 of the instrument shaft 12 by a quick-release lock or the like, and by the reference axial stopper 14a. For this purpose, each instrument shaft 12 includes a grip interface 28 (FIG. 3) for attaching different grips, such as the grips 22a, 22b shown in FIG. 1, for example. Different grips, as used herein, refers to the configuration of the hand grip piece itself. The grip interface 28 of the shaft 12 and the counter piece or fitting slit 40 of the grip are uniformly configured for all grips.

The grips 22a, 22b are connected to the instrument shaft 12 in the manner of a quick-release lock. In the embodiment shown in FIG. 3, the grips have a fitting slit 40 with a ball-thrust piece 40a protruding laterally into the slit. The grips 22a, 22b are coupled to the proximal grip interface 28 on the instrument shaft 12 via the fitting slit 40, such that the ball-thrust piece 40a within the grip latches into a corresponding notch 28a of the grip interface 28. This axially fixes the position of each grip 22a, 22b on the grip interface 28 and also limits the freedom of movement of the reference element adaptor 18 in the axial direction, since the reference element adapter 18 is between the grip 22a, 22b and the reference axial stopper 14a.

In the area of the grip interface 28, the otherwise round instrument shaft 12 can be flattened on one side, for example on the side of the notch 28a, wherein the lo fitting slit 40 then exhibits the same flattening. This prevents the grip 22a, 22b from slipping when torque is transmitted from the grip 22a, 22b to the instrument shaft 12. As should be appreciated, other quick-release locking mechanisms can be employed without departing from the scope of the invention.

If the instrument is a rotationally asymmetrical instrument, such as, for example, an instrument that includes the instrument shafts 12c and 12d (FIG. 1), it also is possible in accordance with the invention to ensure that the instrument always is orientated in the same direction with respect to the reference element adapter 18. This can be achieved by providing an orientating pin 26a at a specific point (defined for example in terms of its angle) in the area of the reference area 14a. The orientating aid, e.g., the orientating pin 26a, is arranged at a particular point on the shaft 12 depending on the instrument shape, e.g., at a particular angular position. This also applies to the orienting slits 26b on the reference element adaptor 18, on which a number of such orienting slits 26b also can be arranged.

With further reference to FIG. 5 and continued reference to FIG. 3, an embodiment of the reference element adaptor 18 is shown that includes four orientating slits 26b, such that the reference element adapter 18 can catch on the rotationally asymmetrical instrument shaft in four pre-set positions. Two of the positions can be seen in more detail in the enlarged representation shown in FIG. 5 and are indicated as 42a and 42b, wherein the orientating pin 26a engages with the corresponding orientating slit 26b. The user can select and set the position, such that the orientation of the reference element adapter 18 in relation to the instrument shaft 12 provides the best visibility of the reference element 20 by the navigation cameras.

Figure 6:
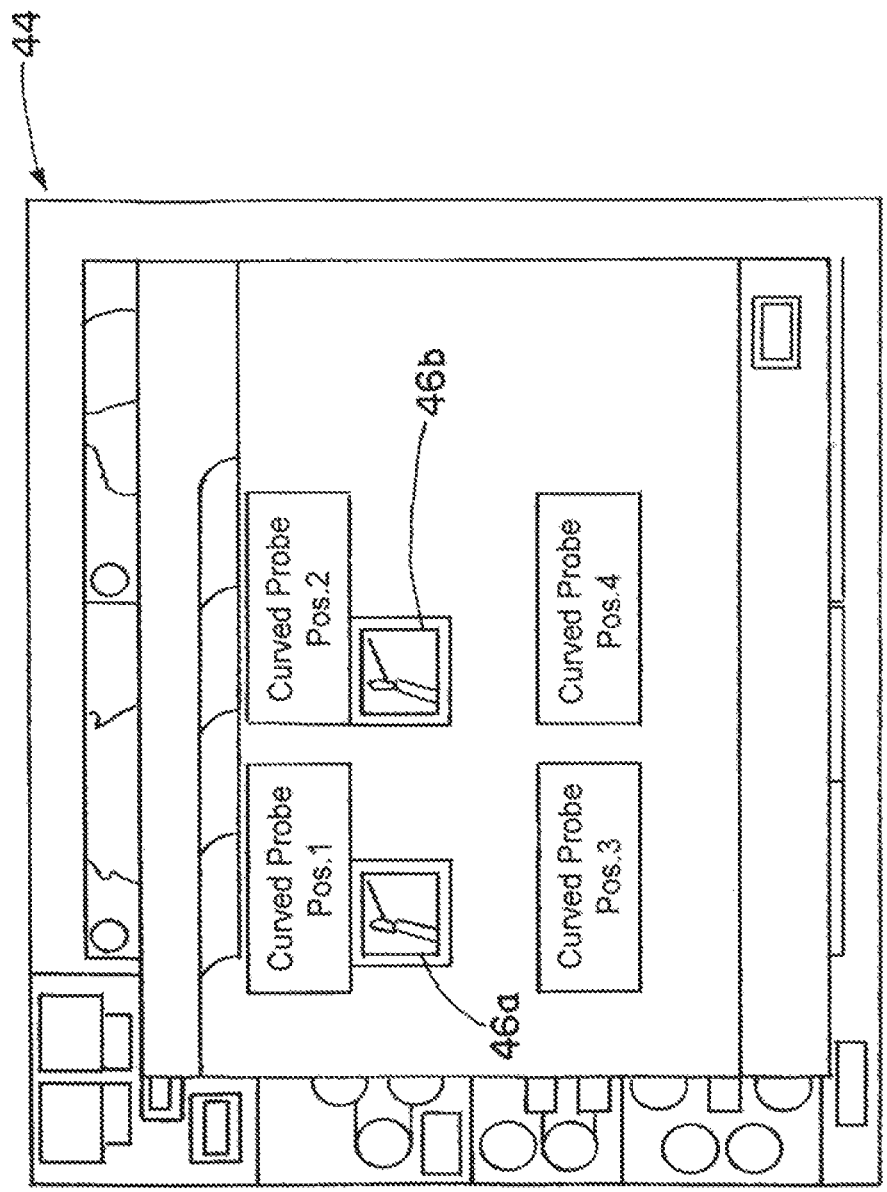
FIG. 6 illustrates a screen shot of software for selecting pre-determined instruments in accordance with an embodiment of the invention.

The orientation of the rotationally asymmetrical instrument shaft relative to the reference element adaptor 18 can be implemented in the computer-guided surgery software for each position, e.g. 42a, 42b. As shown by the screen shot 44 of FIG. 6, the user can select the set instrument position (e.g. 42a (Position 1), 42b (Position 2)) in software via a special selection page for pre-calibrated instruments. In the screen shot 44 of FIG. 6, selection keys 46a, 46b are used to identify to software the orientation of the reference element adapter 18 relative to the instrument shaft. The user makes a selection by clicking on or otherwise identifying the key that corresponds to the selected position of the instrument shaft. By identifying the orientation of the reference element adapter 18 relative to the instrument shaft 12, the orientation of the rotationally asymmetrical instrument can be correctly displayed by the navigation software.

Figure 4:
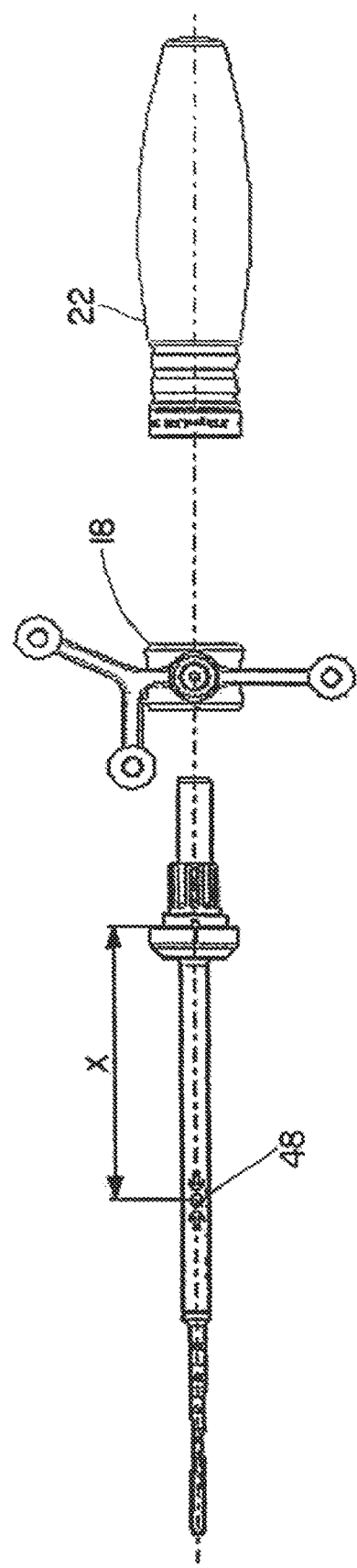
FIG. 4 illustrates a top view of the instrument of FIG. 2.

Referring to FIGS. 2, 4 and 7, computer-guided instrument selection and instrument verification in accordance with the invention will now be discussed. As was noted previously, each instrument or instrument shaft 12 includes a marking point, which, according to one embodiment, is marking point 48. The marking point or indentation 48 can be individually attached to a different side on each instrument shaft and/or can have an instrument-specific distance "X" (FIG. 4) in relation to the reference element and/or in relation to the reference area 14a of the instrument shaft adapting interface 14. The marking point 48 can be tapped by a pointer 50, as is shown in FIG. 7, for example, and the tip of the pointer 50 can be positionally detected by the navigation system. Using the known distance between the tip of the pointer 50 on the marking point 48 and the reference element 20, the instrument can be identified by the software and immediately displayed on a screen in the correct orientation, without manually selecting the instrument via the selection keys. This is advantageous in that the wrong instrument cannot inadvertently be selected or erroneously displayed, since the instrument actually present is automatically verified without requiring direct input from the user.

Furthermore, the marking point 48 also can be used for accuracy verification of the pre-calibrated instrument prior to using the instrument. For example, the tip of the pointer 50 can be placed on the marking point 48 and the position of the tip of the pointer can be displayed on the instrument shaft 12. The displayed position is compared to the actual position. If the pointer is correctly shown by the navigation software having its tip on the marking point 48 then the accuracy is deemed to be sufficiently high, thereby verifying the calibration of the instrument.

Although the invention has been shown and described with respect to a certain preferred embodiment or embodiments, it is obvious that equivalent alterations and modifications will occur to others skilled in the art upon the reading and understanding of this specification and the annexed drawings. For example, although the present invention has been discussed on the basis of example embodiments for spinal instruments, it is not restricted to such instruments but can also be applied to instruments in trauma and orthopaedic (e.g., hip/knee) navigation applications. Accordingly, an instrument set in accordance with the invention can be expanded by new application-specific instruments.

In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

Having thus described the example embodiments, it is now claimed:

1. A reference element adapter apparatus rotatably attachable with a shaft of an associated instrument for use in computer guided surgery, the reference element adapter apparatus comprising:
    a body member comprising a portion configured for selective attachment with an associated reference element, the body member defining an inner axial passageway having a fixed inner diameter,
    wherein the body member is selectively coaxially receivable directly and rotatably on an instrument shaft adapting interface of the shaft of the associated instrument at the fixed inner diameter to provide relative rotatable attachment between the associated instrument and the associated reference element selectively attached with the body member, the reference element adapter apparatus further comprising a mechanical retainer operable to provide selective retention of the instrument shaft of the associated instrument relative to the body member, wherein the mechanical retainer comprises a catch providing a surmountable frictional or positive coupling between the body member and the instrument shaft of the associated instrument, wherein the catch comprises:
        a ball-thrust piece configured to engage a plurality of associated longitudinal notches on the instrument shaft of the associated instrument to inhibit rotation between the body member and the instrument shaft of the associated instrument, or
        a plurality of circumferentially distributed longitudinal notches defined on the inner axial passageway, the plurality of circumferentially distributed longitudinal notches being configured to receive an associated ball-thrust piece carried on the instrument shaft of the associated instrument to inhibit the rotation between the body member and the instrument shaft of the associated instrument.

2. The reference element adapter apparatus of claim 1, further comprising:
    a reference element orientating mechanism operable to selectively fix at least one angular position of the body member relative to the shaft of the associated instrument.

3. The reference element adapter apparatus of claim 2, wherein the reference element orientating mechanism is a selectively operable catch.

4. The reference element adapter apparatus of claim 3, wherein the selectively operable catch comprises one or more of an orientating pin and/or an orientating slit.

5. The reference element adapter apparatus of claim 2 wherein the reference element orientating mechanism comprises an orientating slit defined in the body member, the orientating slit being operable to selectively receive an orientating pin carried by the associated instrument.

6. An apparatus rotatably attachable with a shaft of an associated instrument for use in computer guided surgery, the apparatus comprising:
    a body member defining an inner axial passageway having a fixed inner diameter; and
    a reference element on the body member,
    wherein the body member is selectively coaxially receivable directly and rotatably on an instrument shaft adapting interface of the shaft of the associated instrument at the fixed inner diameter to provide relative rotatable attachment between the associated instrument and the reference element on the body member, the reference element adapter apparatus further comprising a mechanical retainer operable to provide selective retention of the instrument shaft of the associated instrument relative to the body member, wherein the mechanical retainer comprises a catch providing a surmountable frictional or positive coupling between the body member and the instrument shaft of the associated instrument, wherein the catch comprises:

a ball-thrust piece configured to engage a plurality of associated longitudinal notches on the instrument shaft of the associated instrument to inhibit rotation between the body member and the instrument shaft of the associated instrument, or a plurality of circumferentially distributed longitudinal notches defined on the inner axial passageway, the plurality of circumferentially distributed longitudinal notches being configured to receive an associated ball-thrust piece carried on the instrument shaft of the associated instrument to inhibit the rotation between the body member and the instrument shaft of the associated instrument.

7. The apparatus of claim 6, further comprising:

a reference element orientating mechanism operable to selectively fix at least one angular position of the body member relative to the shaft of the associated instrument.

8. The apparatus of claim 7, wherein:

the reference element orientating mechanism is a selectively operable catch comprising one or more of an orientating pin and/or an orientating slit.

9. The apparatus of claim 7, wherein:

the reference element orientating mechanism comprises an orientating slit defined in the body member, the orientating slit being operable to selectively receive an orientating pin carried by the associated instrument.

10. The apparatus of claim 6, wherein the reference element is selectively removable from the body member.

* * * * *